United States Patent [19]

Nakata et al.

[11] Patent Number: 4,896,040

[45] Date of Patent: Jan. 23, 1990

[54] METHOD OF INSPECTING FLOPPY DISK CASING

[75] Inventors: Tomohiro Nakata; Toshihiro Matsushita, both of Kanagawa, Japan

[73] Assignee: Fuji Photo Film Co., Ltd., Kanagawa, Japan

[21] Appl. No.: 140,271

[22] Filed: Dec. 31, 1987

[30] Foreign Application Priority Data

Jan. 9, 1987 [JP] Japan ................................. 62-2898

[51] Int. Cl.$^4$ ................................................ G01J 1/42
[52] U.S. Cl. .................................... 250/372; 356/237
[58] Field of Search ......................... 250/372; 356/237

[56] References Cited

U.S. PATENT DOCUMENTS

| | | | |
|---|---|---|---|
| 3,325,649 | 6/1967 | Bird | 250/372 |
| 3,957,675 | 5/1976 | Schutt | 250/372 |
| 4,511,800 | 4/1985 | Harbeke et al. | 250/372 |
| 4,542,296 | 9/1985 | Kleinnibbelink et al. | 250/372 |
| 4,653,908 | 3/1987 | Yajima et al. | 250/372 |
| 4,659,933 | 4/1987 | Anthon | 250/372 |
| 4,674,875 | 6/1987 | Koizumi | 356/237 |
| 4,752,696 | 6/1988 | Matsushita et al. | 356/446 |
| 4,766,317 | 8/1988 | Harbeke et al. | 250/372 |

FOREIGN PATENT DOCUMENTS 0043503  2/1987  Japan ................................. 250/372

OTHER PUBLICATIONS

Patrick et al., "Surface Defect Analyzer" *IBM Technical Disclosure,* vol. 16, No. 8, Jan. 1974, p. 2694.

*Primary Examiner*—Janice A. Howell
*Assistant Examiner*—William F. Rauchholz
*Attorney, Agent, or Firm*—Sughrue, Mion, Zinn, Macpeak & Seas

[57] ABSTRACT

A light beam containing at least ultraviolet light in a predetermined wave range is projected onto a portion of a floppy disk casing applied with a liner, and ultraviolet light in the predetermined wave range contained in reflected light from each point on the portion of the casing is received. The intensity of the received ultraviolet light corresponding to each point is subjected to a threshold processing and whether the liner is applied to the inner surface of the casing in a satisfactory state is determined on the basis of the result of the threshold processing.

7 Claims, 2 Drawing Sheets

METHOD OF INSPECTING FLOPPY DISK CASING

BACKGROUND OF THE INVENTION

1. Field of the Invention

This invention relates to a method of inspecting a floppy disk casing having a liner applied to the inner surface thereof, and more particularly to a method of inspecting application of the liner to the casing.

2. Description of the Prior Art

Generally, a floppy disk is loaded in a recording and reproducing system as it is accommodated in a thin casing made of plastic or the like. Any dust deposited on the disk surface will adhere to the magnetic had, adversely affecting recording and reproduction. Accordingly, a cleaning liner generally made of non-woven fabric obtained by bonding together fibers of rayon, nylon, PET, polypropylene or the like (several tens of micrometers to several hundreds of micrometers in thickness) is applied to the inner surface of the casing to remove dust on the disk as the disk is rotated for recording or reproduction. The casing is for accommodating therein the floppy disk and is generally referred to as a "shell" or "jacket".

The liner must be applied to the inner surface of the casing in a predetermined position, otherwise the cleaning effect of the liner may be lowered or the liner may damage the disk. Accordingly, application of the liner is inspected during the manufacturing step of the floppy disk, i.e., to check whether the liner is applied to the inner surface of the casing in a satisfactory state.

In accordance with a conventional method of inspection, before the casing halves are connected together, visible light is projected onto each casing half from the liner side and reflected light from the casing half is received by a light receiving means such as an industrial television camera to obtain image signals by way of photoelectric conversion. The intensity distribution of the image signals thus obtained is subjected to threshold processing and whether the liner is applied to the inner surface of the casing in a satisfactory state is determined on the basis of the result of the threshold processing. However, since the difference in light absorption between the liner and the casing is small, especially when the liner and the casing are of similar colors, it is very difficult to determine whether application of the liner is satisfactory without disturbance arising from noise.

SUMMARY OF THE INVENTION

In view of the foregoing observations and description, the primary object of the present invention is to provide a method of inspecting application of the liner to the casing wherein whether application of the liner is satisfactory may be detected more precisely without disturbance arising from noise.

In accordance with the present invention, a light beam containing at least ultraviolet light in a predetermined wave range is projected onto a portion of the casing applied with the liner, and ultraviolet light in the predetermined wave range contained in reflected light from each point on the portion of the casing is received, and the intensity of the received ultraviolet light corresponding to each point is subjected to threshold processing and whether the liner is applied to the inner surface of the casing in a satisfactory state is determined on the basis of the result of the threshold processing.

That is, we have found that the light absorptions of the casing and the liner change by a large amount in the ultraviolet range or in the region of the boundary between the ultraviolet light range and the visible light range with the light absorptions being increased on the shorter wave length side, and that the wave length at which the light absorption of the casing changes by a large amount differs from that of the liner owing to the differences in material, surface conditions and the like. When the relation between the light absorption of the casing and the wave length and that between the light absorption of the liner and the wave length are plotted on a graph with the wave length as the axis of the abscissas and the light absorption as the axis of the ordinates, there exists, in an ultraviolet light range, a wave range in which the light absorption of one of the casing and the liner has increased with the light absorption of the other remaining low. Accordingly, when light in such a wave range is used for inspecting the application of the liner, the difference in intensity between reflected light from the casing and reflected light from the liner can be enhanced, whereby existence of the liner at each point of the casing can be precisely determined with noise having little effect on the enhancement of the intensity difference. This determination can be obtained irrespective of the colors of the liner and the casing, and accordingly, in accordance with the method of the present invention, whether application of the liner is satisfactory can be precisely detected even if the colors of the casing and the liner are similar to each other.

The term "threshold processing" refers to processing in which the intensity of the received ultraviolet light corresponding to each point is compared with a predetermined threshold level or a reference value and whether it is the casing or the liner that is reflecting the ultraviolet light is determined on the basis of the result of the comparison. For example, when the intensity is higher than the predetermined threshold level, it is determined that the ultraviolet light is reflected by the liner on the casing. Generally, the intensity of the ultraviolet light is converted into an electrical signal and then is subjected to the threshold processing.

Whether or not application of the liner is satisfactory may be determined by, for example, visually inspecting a visible image formed on the basis of the result of the threshold processing, or by calculating the area of the region determined to be applied with the liner and/or the center of gravity of the portion.

A light beam containing at least ultraviolet light in a predetermined wave range may be projected onto the surface to be inspected simultaneously to irradiate the entire area of the surface, or may be projected to scan the surface. In the former case, it is preferred that the reflected light be received by a one-dimensional or two-dimensional photoelectric converter element or photoelectric converter tube which can separately extract the intensities of the ultraviolet light corresponding to the points on the surface.

DESCRIPTION OF THE PREFERRED EMBODIMENT

Figure 1:
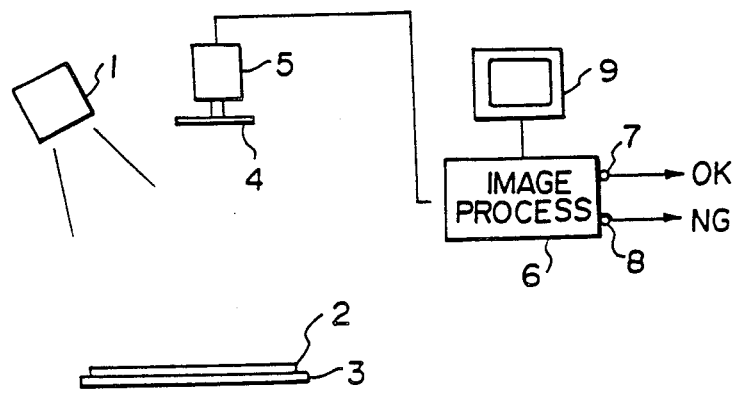
FIG. 1 is a schematic view showing an example of a system for carrying out the method of the present invention.
Figure 2:
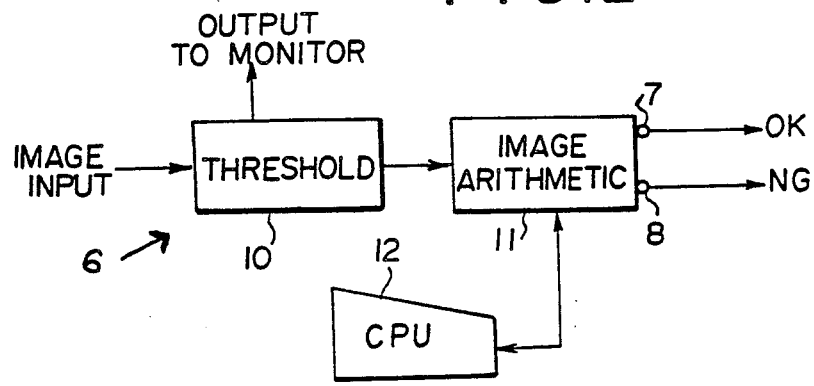
FIG. 2 is a view for illustrating in detail a part of the system shown in FIG. 1.

In FIG. 1, light containing ultraviolet light is emitted from a light source 1 and projected on a casing half 3 applied with a liner 2. Reflected light from the casing half 3 is received through an ultraviolet transmission filter 4 by a TV camera 5 having a built-in CCD (charge coupled device) sensitive to ultraviolet light. Image signals obtained through photoelectric conversion by the CCD are input into an image processing section 6 to be subjected to threshold processing therein. The image processing section 6 further performs a predetermined arithmetic on the basis of the result of the threshold processing to determine whether the liner is applied to the casing in a satisfactory state. When the image processing section 6 determines that the liner is applied to the casing in a satisfactory state, an OK pulse signal is output from an OK signal output terminal 7, and otherwise, a NG (no good) signal is output from a NG signal output terminal 8. Further, the image processing section 6 delivers signals corresponding to the result of the threshold processing to a monitor 9 which displays the region of the casing applied with the liner. As shown in FIG. 2, the image processing section 6 comprises a threshold processing section 10 which compares intensities of input image signals with a reference value one after another to binary-code them, an image arithmetic section 11 which calculates at high speed the area, the circumference length, the center of gravity and the like of the region determined to be the liner region by the threshold processing section 10, determines whether the application of the liner is satisfactory on the basis of the result of the calculation and selectively outputs the OK signal or the NG signal according to the determination, and a CPU (central processing unit) 12 which controls the image arithmetic section 11.

Figure 3:
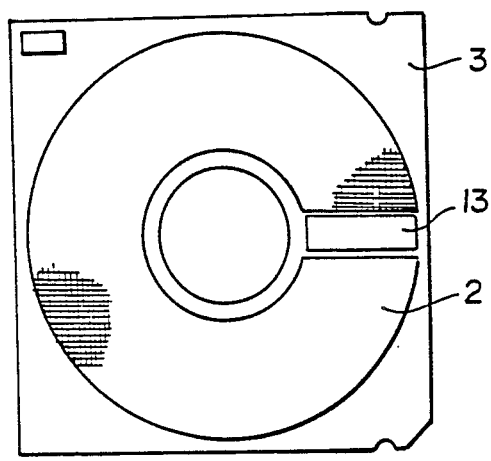
FIG. 3 is a plan view showing the relation between the casing and the liner.

The liner 2 is applied to the casing half 3 to cover a predetermined region of the inner surface of the casing half 3 with an area opposed to a magnetic head access opening 13 being opened to give the magnetic head access to the floppy disk as shown in FIG. 3. The liner 2 may be applied to either both the casing halves or one of the casing halves. The system shown in FIG. 1 is for detecting whether the liner 2 is in place in the casing half 3.

Figure 4:
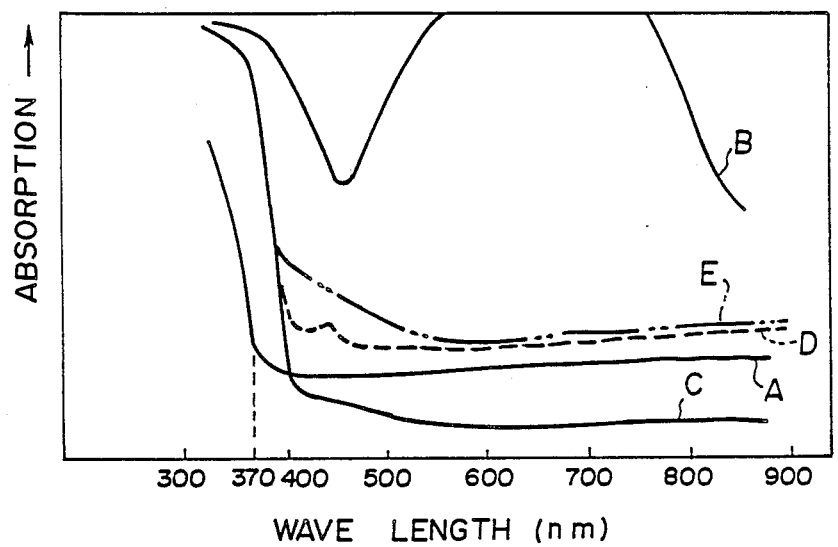
FIG. 4 is a graph showing the light absorption characteristics of the casing and the liner.

Light absorptions of the liner and the casing change with changes in wave length as shown in FIG. 4. In FIG. 4, light absorption characteristics of a white liner, a blue casing half, a white casing half, a gray casing half, and a beige casing half are respectively shown by curves A to E. As can be understood from FIG. 4, for visible range light (having a wave length of about 400 nm to 750 nm), the difference in light absorption between the white liner and the blue casing half, and accordingly, the difference between the intensity of light reflected from the white liner and the intensity of light reflected from the blue casing half, is large, while the difference in light absorption between the white liner and the white casing, the gray casing or the beige casing is too small to precisely distinguish the liner from the casing half unless the S/N ratio is excellent. On the other hand, for ultraviolet range light (having wave lengths shorter than about 400 nm), the light absorption of the white, gray and beige casing halves is suddenly increased in the wave range shorter than about 400 nm while the light absorption of the white liner is suddenly absorbed in the wave range shorter than about 370 nm. Accordingly, in the wave range between about 370 nm and 400 nm, the difference between the light absorption of the casing half and that of the liner, i.e., the difference between the intensity of reflected light from the casing half and that of reflected light from the liner, is very large. The light source 1 emits light containing 370 nm to 400 nm wave length ultraviolet light.

The light source 1 may be either one which mainly emits ultraviolet light in said wave range, or one which emits light containing at least ultraviolet light in said wave range. The former type of light source may comprise a lamp mainly emitting ultraviolet light in said wave range or may comprise a lamp emitting light containing ultraviolet light in said wave range and other light and a filter which mainly transmits ultraviolet light in said wave range. When the former type light source is used, the light receiving means (comprising the ultraviolet transmission filter 4 and the TV camera 5 in the illustrated embodiment) may be one having sensitivity mainly to ultraviolet light in said wave range, or one having sensitivity to ultraviolet light in said wave range and to other light. The former type light receiving means may comprise a light receiving element having sensitivity mainly to the ultraviolet light in said wave range, or may comprise a light receiving element having sensitivity to ultraviolet light in said wave range and to other light and a filter which mainly transmits ultraviolet light in said wave range. When the latter type light source is used, the light receiving means should be one having sensitivity mainly to ultraviolet light in said wave range.

For a long light-source life, it is preferred that the light source comprises a xenon stroboscope.

We claim:

1. A method of inspecting a floppy disk casing comprising the steps of projecting a light beam containing at least ultraviolet light in a predetermined wave range onto a portion of an inner surface of the casing applied with a liner;

receiving ultraviolet light in the predetermined wave range contained in reflected light from each point on a portion of the casing or the liner;

subjecting the intensity of the received ultraviolet light, corresponding to each point on the portion of the casing or the liner, to a threshold processing; and differentiating the intensity of the received ultraviolet light corresponding to the casing from the intensity of the received ultraviolet light corresponding to the liner to determine whether the liner is applied to the inner surface of the casing in a satisfactory state on the basis of a result of the threshold processing.

2. A method of inspecting a floppy disk casing as defined in claim 1 in which said light beam is emitted from a light source which emits light containing ultraviolet light in said predetermined wave range and other light, and ultraviolet light in the predetermined wave range contained in reflected light is received by a light receiving means having sensitivity to ultraviolet light in said predetermined wave range.

3. A method of inspecting a floppy disk casing as defined in claim 2 in which said light source comprises a lamp emitting light containing ultraviolet light in said predetermined wave range and other light, and a filter which transmits only ultraviolet light in said predetermined wave range.

4. A method of inspecting a floppy disk casing as defined in claim 2 in which said light receiving means comprises a light receiving element having sensitivity to ultraviolet light in said predetermined wave range and to other light, and a filter which transmits only ultraviolet light in said predetermined wave range.

5. A method of inspecting a floppy disk casing as defined in claim 1 in which said light beam is emitted from a light source which emits light containing ultraviolet light in said predetermined wave range and other light, and ultraviolet light in the predetermined wave range contained in reflected light is received by a light receiving means having sensitivity mainly to ultraviolet light in said predetermined wave range.

6. A method of inspecting a floppy disk casing as defined in claim 1, 2, 3, 4 or 5 in which said predetermined wave range is from 370 nm to 400 nm.

7. A method of inspecting a floppy disk casing comprising the steps of: projecting a light beam, containing ultraviolet light in the 370 nm to 400 nm wave range, onto a portion of an inner surface of the casing applied with a liner; receiving ultraviolet light in the 370 nm to 400 nm wave range contained in reflected light from each point on the portion of the casing or the liner;

converting to an electrical signal the intensity of the received ultraviolet light corresponding to each point on the portion of the casing or the liner;

subjecting the electrical signal to a threshold processing;

differentiating the electrical signal, representing the intensity of the received ultraviolet light corresponding to the casing, from the electrical signal representing the intensity of the received ultraviolet light corresponding to the liner; and calculating the area, the circumference length and the center of gravity of the portion of the liner to determine whether the liner is applied to the inner surface of the casing in a satisfactory state on the basis of a result of the threshold processing.

* * * * *